United States Patent
Steward et al.

(10) Patent No.: US 9,228,209 B2
(45) Date of Patent: Jan. 5, 2016

(54) METHOD FOR PRODUCING TRIPTOLIDE

(75) Inventors: Nicolas Steward, Pins-Justaret (FR);
Nadine Chomarat, Fayssac (FR); Ngoc Thien N'Guyen, Rouffiac Tolosan (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 594 days.

(21) Appl. No.: 13/508,068

(22) PCT Filed: Nov. 5, 2010

(86) PCT No.: PCT/EP2010/066916
§ 371 (c)(1),
(2), (4) Date: May 4, 2012

(87) PCT Pub. No.: WO2011/054929
PCT Pub. Date: May 12, 2011

(65) Prior Publication Data
US 2012/0225936 A1 Sep. 6, 2012

(30) Foreign Application Priority Data
Nov. 5, 2009 (FR) ..................... 09 57847

(51) Int. Cl.
| | | |
|---|---|---|
| *C12N 5/00* | (2006.01) | |
| *C12N 5/02* | (2006.01) | |
| *C12P 17/16* | (2006.01) | |
| *A01N 65/00* | (2009.01) | |
| *A61K 36/37* | (2006.01) | |
| *C12P 5/00* | (2006.01) | |
| *A61K 31/365* | (2006.01) | |
| *C12P 17/18* | (2006.01) | |

(52) U.S. Cl.
CPC ................. *C12P 5/00* (2013.01); *A61K 31/365* (2013.01); *A61K 36/37* (2013.01); *C12P 17/18* (2013.01); *C12P 17/181* (2013.01)

(58) Field of Classification Search
None
See application file for complete search history.

(56) References Cited

U.S. PATENT DOCUMENTS

| | | | |
|---|---|---|---|
| 4,328,309 A | 5/1982 | Chalmers et al. | |
| 6,069,009 A * | 5/2000 | Pepin et al. | 435/420 |
| 6,303,589 B1 * | 10/2001 | Glinski et al. | 514/169 |
| 7,879,369 B2 * | 2/2011 | Koepke et al. | 424/725 |

FOREIGN PATENT DOCUMENTS

| | | |
|---|---|---|
| CN | 101358180 A | 2/2009 |
| JP | 57002699 | 1/1982 |
| JP | 58-5196 A | 1/1983 |
| WO | WO 97/44476 | 11/1997 |
| WO | WO 98/13057 | 4/1998 |
| WO | WO 2005/012507 A1 | 2/2005 |

OTHER PUBLICATIONS

Brinker et al., "Medicinal chemistry and pharmacology of genus *Tripterygium* (Celastraceae)", Phytochemistry, vol. 68 (2007) pp. 732-766.
Dharmananda et al., "Tripterygium", Institute for Traditional Medicine, (1996) pp. 1-2.
Dujack et al., "47. Antineoplastic Diterpenes in Tripterygium wilfordii Tissue Culture. The Effects of Precursors on Diterpene Production", Annual Meeting Abstracts, vol. 16 (1980) p. 216.
Kutney et al. "Studies with plant-cell cultures of the Chinese herbal plant, Triptergium wilfordii. Isolation and characterization of diterpenes", Recl. Trav. Chim. Pays-Bas, vol. 115 (1996) pp. 77-93.
Kutney et al., "Cultivation of Tripterygium wilfordii Tissue Cultures for the Production of the Cytotoxic Diterpene Tripdiolide", J. of Medicinal Plant Research, vol. 48, (1983) pp. 158-163.
Kutney et al., "Cytotoxic diterpenes triptolide, tripdiolide, and cytotoxic triterpenes from tissue cultures of Tripterygium wilfordii", Can. J. Chem., vol. 59 (1981) pp. 2677-2683.
Kutney et al., "Studies with Plant Cell Cultures of the Chinese Herbal Plant, Tripterygium wilfordii, Synthesis and Biotransformation of Diterpene Analogues", Heterocycles, vol. 44, No. 1 (1997) pp. 95-104.
Kutney et al., "Studies with tissue cultures of the Chinese herbal plant, Tripterygium wilfordii. Isolation of metabolites of interest in rheumatoid arthritis, immunosuppression, and male contraceptive activity", Can. J. Chem., vol. 70 (1992) pp. 1455.
Samija, "Enhanced Yield of Medicinal Products from Tripterygium Cell Cultures", The University of British Columbia (1992) pp. I-IV.
Takayama, "XXVII Tripterygium wilfordii: In Vitro Culture and the Production of the Anticancer Compounds Tripdiolide and Triptolide", Biotechnology in Agriculture and Forestry, vol. 28 (1994) pp. 457-468.
Tao et al., "Effective Therapy for Nephritis in (NZB X NZW)F1 Mice with Triptolide and Tripolide, the Principal Active Components of the Chinese Herbal Remedy Tripterygium wilfordii Hook F", Arthritis & Rheumatism, vol. 58, No. 6 (2008) pp. 1774-1783.
Tao et al., "The Chinese Anti-Inflammatory and Immunosuppressive Herbal Remedy Tripterygium wilfordli Hook F", Rheumatic Disease Clinics of North America, vol. 26, No. 1 (2000) pp. 29-50.
Wenyan et al., "Tripterygium in Dermatologic Therapy", International Journal of Dermatology, vol. 24, No. 3(1985) pp. 152-157.
WPI Thomson Scientific Database Abstract No. XP-002592589 abstract of Chinese Publication CN200810177697 published Mar. 13, 2008.

(Continued)

*Primary Examiner* — Chris R Tate
*Assistant Examiner* — Douglas F White
(74) *Attorney, Agent, or Firm* — Birch, Stewart, Kolasch & Birch, LLP

(57) ABSTRACT

The invention relates to a method for producing triptolide from a suspension cell culture of *Tripterygium* sp., to a triptolide-enriched extract obtainable by means of extraction from the culture medium of an in vitro culture of dedifferentiated cells of the species *Tripterygium*, and to the therapeutic applications of said extract.

15 Claims, 11 Drawing Sheets

(56) References Cited

OTHER PUBLICATIONS

Figure 1:
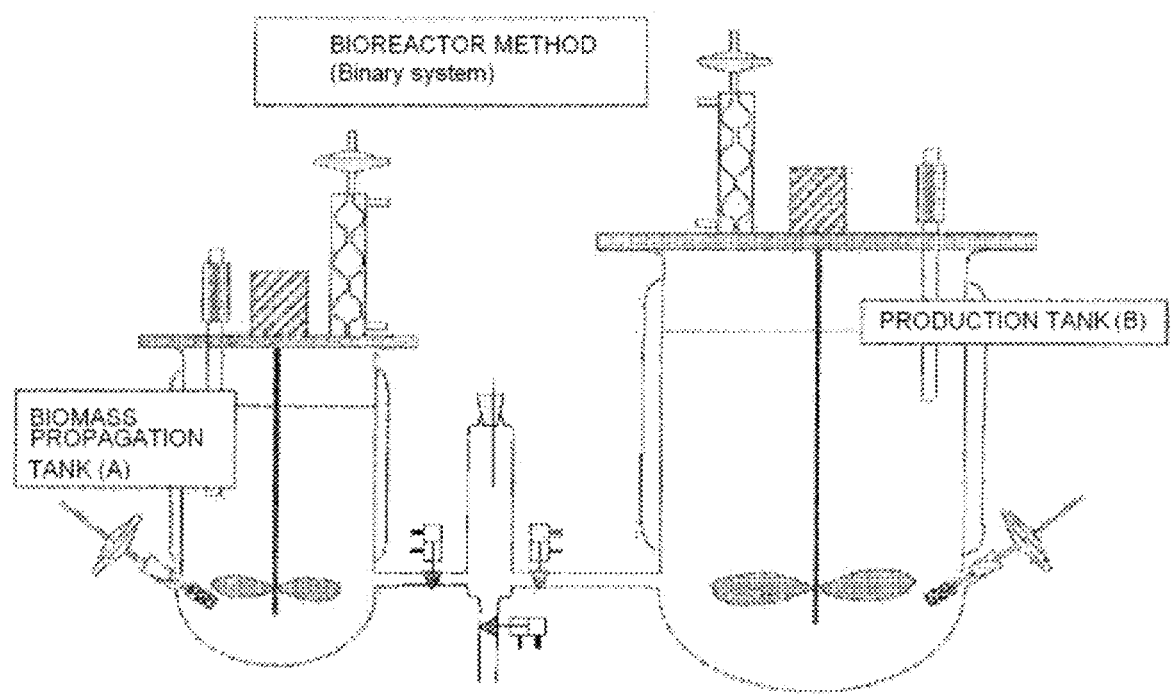

WPI Thomson Scientific Database Abstract No. XP-002592590 abstract of Chinese Publication CN20021000774 published on Jan. 25, 2002.

WPI Thomson Scientific Database Abstract No. XP-002592591 abstract of Japanese Publication JP19810102096 published on Jun. 30, 1981.

Feng et al., "Inhibition of the Nuclear Factor-κB Signaling Pathway by Leflunomide or Triptolide also Inhibits the Anthralin-Induced Inflammatory Response but Does Not Affect Keratinocyte Growth Inhibition," Biological & Pharmaceutical Bulletin, vol. 28, No. 9, Sep. 2005, pp. 1597-1602.

* cited by examiner

METHOD FOR PRODUCING TRIPTOLIDE

The invention relates to a method for producing triptolide from a cell suspension culture of *Tripterygium* sp., for example *Tripterygium wilfordii*.

Triptolide, a diterpene triepoxide, is a compound purified from *Tripterygium wilfordii*. This plant has been used for more than four centuries in traditional Chinese medicine to treat autoimmune diseases and inflammatory diseases, in particular rheumatoid arthritis. Recently, the powerful anticancer activity of triptolide has also been discovered. Antiproliferative and proapoptotic activities were shown in various types of cancer cells in vitro and in vivo. Clinical trials were undertaken to study the treatment of rheumatoid arthritis and advanced-stage cancer, for example leukemia. A recent publication (Brinker A M et al., Phytochemistry 68 (2007) 732-766) summarizes the pharmacological properties of triptolide and derivatives thereof from *Tripterygium wilfordii*.

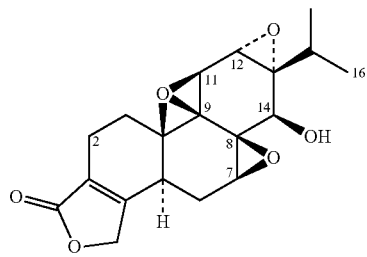

Chemical Structure of Triptolide

Triptolide is a secondary metabolite belonging to the family of diterpenes which are naturally present in very small quantities in the bark and the aerial parts of the plant, but more in the roots (average concentration=10 ppm).

The chemical synthesis of triptolide is very difficult because it requires the implementation of a process comprising roughly 20 steps.

Currently, triptolide is provided by the company Pharmagenesis. It is produced by extraction of *Tripterygium wilfordii* roots and purification by two chromatographic steps. This process is long and complex.

The extraction/purification yield from roots, for example, is 0.0005%.

10 to 15 years are required for the plant to fully mature before being harvested; production of triptolides from the mature plant leads to the plant's destruction. In the context of ecological sustainable development, it is thus necessary to provide an alternative method for triptolide production that enables a yield suitable to industrial production of the compound of interest.

Kutney J P at al. disclose a method for preparing a *Tripterygium wilfordii* leaf cell suspension culture and a method for separating triptolide and derivatives thereof from said culture (Can J Chem 58 (1981): 2677-2683). However, production yields are even lower than those of the traditional method.

Application CN101358180A, published on Feb. 4, 2009, describes a method for preparing a stem cell suspension culture. These cells were generated from *Tripterygium wilfordii* roots. The stated triptolide production reached 0.027 mg/l per day. The authors of this patent describe, among other things, a method comprised of a cell propagation medium, a triptolide production medium and a total alkaloids production medium. However, said application does not employ, as described in the present invention, an abiotic elicitor of terpene biosynthesis precursors or a hormonal elimination step.

The present invention provides a method for producing triptolide from stem cells of aerial parts of *Tripterygium wilfordii* with a high yield suitable to industrial production.

The present invention also provides the culture media that made it possible to achieve this particularly advantageous yield.

Indeed, the Inventors observed, in a surprising manner, a triptolide yield of 3 mg/l of culture per day. This yield is 110 times higher than the best overall yield described in application CN101358180A: 73 times higher than the best yield in the supernatant and 127 times higher than the best yield expressed in weight percent of triptolide in relation to the weight percent of dry biomass.

In a surprising manner, the Inventors also showed that a triptolide-enriched extract obtained by said method inhibits the activation of transcription factor NFκB by TNFα in an equivalent manner to pure triptolide.

The Inventors also showed that a triptolide-enriched extract obtained according to the method of the invention inhibits the production of $NO_2^-$ induced by lipopolysaccharides more effectively than pure triptolide.

The Inventors showed that a triptolide-enriched extract obtained according to the method of the invention inhibits the influx of intracellular calcium induced by the specific stimulation of protease-activated receptor 2 (PAR-2) by trypsin.

These three tests validate the anti-inflammatory activity of a triptolide-enriched extract obtained according to the method of the invention.

This activity is confirmed at the cutaneous level in models of atopic dermatitis and psoriasis using PCR arrays.

The invention consequently relates to a method for producing triptolide from a cell suspension culture of the aerial parts of *Tripterygium* sp., for example *Tripterygium wilfordii*, *Tripterygium regelii*, or *Tripterygium hypoglaucum* or plants of the family of Celastraceae. In one embodiment of the invention, the method for producing triptolide is carried out from a cell suspension culture of aerial parts, for example stems, petioles, leaves and/or inflorescences.

The present invention relates to a method for producing triptolide in culture medium from a cell culture of the species *Tripterygium* comprising the following steps:
(i) a phase of production of a biomass of dedifferentiated cells of the species *Tripterygium*, for example derived from calluses, in one or several nutrient media for propagation under biomass growth conditions,
(ii) a phase of hormonal elimination of the cell cultures obtained in step (i) in an elimination medium substantially free of auxins,
(iii) a phase of elicitation by the addition of an elicitation cocktail to the cells of step (ii) in elimination medium,
(iv) preparation of a triptolide-enriched extract from the culture medium at the end of step (iii).

The elicitation phase rests on adding the elicitation cocktail to the elimination medium containing the separated biomass produced in step (ii) and then culturing; triptolide production takes place in said culture medium. The elicitation phase in the context of the present invention thus corresponds to the triptolide production phase.

According to the present invention, the elicitation cocktail used in the method comprises:
a) at least one cellular differentiation factor of plant cells, for example a cytokinin, for example selected from benzylaminopurine (BAP), abscisic acid, kinetin, thidiazuron, 6-γ-γ-dimethylallylaminopurine, zeatin or isopentenyladenine, or a gibberellin;

b) at least one stressing agent, for example an abiotic elicitor, and
c) at least one precursor of the terpene synthesis pathway, for example of the triptolide synthesis pathway, for example geraniol, farnesol, including pyrophosphate forms thereof, sodium acetate, pyruvic acid or mevalonic acid.

Preferentially, step (i) of the method of the invention is preceded by the following steps:
(α) Inducing calluses from an explant of tissue from the aerial part of *Tripterygium wilfordii* by culturing on an agar medium comprising cell dedifferentiation inducers,
(β) Suspending the callus cells obtained in step (i) and propagating the suspension cells in propagation medium.

"Aerial parts" refer to the parts of the plant located above ground, for example leaves, stems, petioles and/or inflorescences.

According to the present invention, said method can also be applied to any other part of the plant such as seeds and roots.

Step (α) of the inventive method consists of producing calluses from a tissue explant, for example an explant of the aerial parts of *Tripterygium wilfordii*, for example a piece of leaf roughly 1 cm² in size, cultured on an agar medium comprising dedifferentiation inducers.

According to one embodiment of the invention, the aerial part(s) of *Tripterygium wilfordii* include(s) leaves, stems, petioles and/or inflorescences.

"Callus" refers to a cluster of dedifferentiated cells, also called stem cells.

The dedifferentiation medium is, for example, a medium comprising:
at least one macroelement, for example selected from $NH_4NO_3$, $KNO_3$, $CaCl_2.2H_2O$, $MgSO_4.7H_2O$, $KH_2PO_4$, for example at a concentration of up to 6000 mg/l,
at least one microelement, for example KI, $H_3BO_3$, $MnSO_4.4H_2O$, $ZnSO_4.H_2O$, $Na_2MoO_4.2H_2O$, $CuSO_4.5H_2O$, $CoCl_2.6H_2O$, $FeSO_4.7H_2O$, $Na_2EDTA.2H_2O$, for example at a total microelement concentration in said medium of up to 200 mg/l of culture medium,
at least one vitamin, for example myo-inositol, nicotinic acid, pyridoxine-HCl or thiamine-HCl, for example at a concentration of up to 3 g/l of culture medium,
at least one amino acid, for example at a concentration in the culture medium of up to 3 g/l, for example glycine,
at least one source of carbon, for example sucrose, for example at a concentration of 20-70 g/l of culture medium, for example 30 g/l,
at least one hormone, preferably a plant hormone, or growth factor, preferably a plant growth factor, or growth regulator, preferably a plant growth regulator, for example kinetin, 2,4-dichlorophenoxyacetic acid (2,4-D) or naphthalene acetic acid (NAA), for example at a concentration of 0.001-10 mg/l of culture medium, for example 0.1-3 mg/l of culture medium.

Compositions of the dedifferentiation medium and the use thereof are given in the examples.

The pH of said medium is adjusted, for example to pH 6±0.5, and it is autoclaved at 121° C. for at least 20 minutes or by filtration at 0.2 μm.

Incubation can take place in the dark, for example at a temperature of roughly 25-30° C., for example at 27° C. or 28° C.

The dedifferentiation medium is, for example, a solid medium, for example gelled by adding 8-12 g/l of agar, for example 8 g/l.

Step (β) of the inventive method consists of suspending dedifferentiated cells from calluses obtained in the first step in a liquid culture medium and propagating the cells of the suspension. Culturing takes place for a period of 10-30 days, for example 15-20 days, for example at a temperature of roughly 27° C. Culturing takes place in the dark and with agitation.

The culture medium of this step (β) is, for example, cell propagation medium, for example adjusted to pH 6 and sterilized by autoclaving at 121° C. for at least 20 minutes or by sterile filtration at 0.2 μm.

The cell propagation medium is a medium comprising:
at least one macroelement, for example selected from $NH_4NO_3$, $KNO_3$, $CaCl_2.2H_2O$, $MgSO_4.7H_2O$, $KH_2PO_4$, for example at a concentration of up to 6000 mg/l,
at least one microelement, for example KI, $H_3BO_3$, $MnSO_4.4H_2O$, $ZnSO_4.H_2O$, $Na_2MoO_4.2H_2O$, $CuSO_4.5H_2O$, $CoCl_2.6H_2O$, $FeSO_4.7H_2O$, $Na_2EDTA.2H_2O$, for example at a total microelement concentration in said medium of up to 200 mg/l of culture medium,
at least one vitamin, for example myo-inositol, nicotinic acid, pyridoxine-HCl, thiamine-HCl, for example at a concentration of up to 3 g/l of culture medium,
at least one amino acid, for example at a concentration in the culture medium of up to 3 g/l, for example glycine,
at least one source of carbon, for example sucrose, for example at a concentration of 30 g/l,
at least one hormone, preferably a plant hormone, or growth factor, preferably a plant growth factor, or growth regulator, preferably a plant growth regulator, for example kinetin, 2,4-dichlorophenoxyacetic acid (2,4-D), naphthalene acetic acid (NAA), for example at a concentration of 0.001-10 mg/l of culture medium, for example 0.1-3 mg/l of culture medium.

An example of propagation medium and the use thereof is provided in the examples.

A propagation medium is, for example, the medium of example 2.

According to an alternative of the invention, the steps of both dedifferentiation (α) and/or propagation (β) can be carried out in propagation medium or dedifferentiation medium.

Step (i) of the inventive method consists of the production of biomass from dedifferentiated cells, for example cells of the suspension obtained in step (β), in a suitable nutrient medium, for example the propagation medium described above. It lasts for 10-30 days. It is carried out preferably at 27-28° C.

During this step, the cells are regularly transplanted or propagated, for example, every 7-10 days. Transplantation consists in diluting part of the cell culture in new medium. For example, ⅕ of the culture is suspended in a volume of new medium corresponding to the volume of the initial culture. This enables the cell line to be maintained in liquid medium.

Similarly, the quantity of biomass can be increased by using a whole culture to inoculate a new nutrient medium, the inoculum representing roughly ⅕ of the final culture volume.

Step (ii) of the inventive method consists of a hormonal elimination step, for example for a period of 5-15 days, for example roughly 7 days.

The objective of hormonal elimination is to eliminate auxin(s), such as growth hormone 2,4-D and/or NAA, present in the culture or propagation medium. This step makes it possible to obtain metabolic synchronization of the cells, i.e., derepression of the terpene biosynthesis pathway.

The hormonal elimination medium is a medium free of auxins, for example free of 2,4-D and NAA, or a medium substantially free of auxins, for example a medium wherein 2,4-D and NAA are each present at a concentration lower than 0.01 mg/l of culture medium.

The elimination medium has the following composition:
- at least one macroelement, for example selected from $NH_4NO_3$, $KNO_3$, $CaCl_2.2H_2O$, $MgSO_4.7H_2O$, $KH_2PO_4$ or sodium pyruvate, for example at a concentration of up to 7000 mg/l,
- at least one microelement, for example KI, $H_3BO_3$, $MnSO_4.4H_2O$, $ZnSO_4.H_2O$, $Na_2MoO_4.2H_2O$, $CuSO_4.5H_2O$, $CoCl_2.6H_2O$, $FeSO_4.7H_2O$, $Na_2EDTA.2H_2O$, for example at a total microelement concentration in said medium of up to 200 mg/l of culture medium,
- at least one vitamin, for example myo-inositol, nicotinic acid, pyridoxine-HCl, thiamine-HCl or glycine, for example at a concentration of up to 60 mg/l of culture medium,
- at least one source of carbon, for example sucrose, for example at a concentration of 20-70 g/l, for example 30 g/l,
- at least one hormone, preferably a plant hormone, or growth factor, preferably a plant growth factor, or growth regulator, preferably a plant growth regulator, for example kinetin or indole-butyric acid (IBA), for example at a concentration of 0.001-10 mg/l of culture medium, for example 1-3 mg/l of culture medium.

An elimination medium of the invention is, for example, the elimination medium whose composition is indicated in example 3. The pH of the medium is adjusted, for example to pH 6±0.5, and it is sterilized by a suitable means.

The elicitation phase of step (iii) of the inventive method makes it possible to induce triptolide production from the eliminated cell culture. The elicitation phase is also the triptolide production phase. It lasts 15-35 days, for example 20-25 days.

The Inventors indeed observed that cell division and triptolide production are not concomitant. Surprisingly, they are even incompatible. To resolve this problem, the Inventors developed a hormonal elimination step and a cocktail of elicitors that stops cell division, induces cellular stress, which activates biochemical defense pathways causing triptolide production, and provides precursors of the terpene biosynthesis pathway.

According to the present invention, said cocktail does not contain auxins, for example it does not contain 2,4-D, or does not contain NAA, or does not contain either of the two products.

According to one embodiment of the invention, said cocktail comprises:
1) at least one cellular differentiation factor of plant cells, for example a cytokinin or a gibberellin, for example benzylaminopurine (BAP),
2) at least one stressing agent or "elicitor", for example of chemical or "abiotic" origin, for example 5-chlorosalicylic acid (5-chloro SA), salicylic acid, acetylsalicylic acid (ASA) and/or methyl jasmonate (MeJA),
3) at least one precursor of terpene synthesis such as, for example, farnesol, geraniol, sodium acetate, pyruvic acid or mevalonic acid.

In the context of the present invention, a cytokinin is, for example, abscisic acid, benzylaminopurine, zeatin, kinetin, thidiazuron, isopentenyladenine, 6-γ-γ-dimethylallylaminopurine or a gibberellin.

BAP, for example, is used at a concentration of 0.01-5 mg/l of culture medium, for example 0.5-5 mg/l.

5-Chlorosalicylic acid (5-chloro SA), for example, is used at a concentration of 0.1-15 mg/l of culture medium.

Salicylic acid, for example, is used at a concentration of 0.1-100 mg/l of culture medium, for example 20-60 mg/l, for example 45 mg/l of culture medium.

Farnesol is present at a concentration of 1-100 mg/l of culture medium, for example 15-30 mg/l, for example 30 mg/l of culture medium.

Geraniol is present at a concentration of 1-100 mg/l of culture medium, for example 20-30 mg/l.

Methyl jasmonate (MeJA) is present at a concentration of 1-100 mg/l.

Said elicitor cocktail has a triple action: it reorients cells toward cellular differentiation, for example roots; it generates cellular stress and thus activates genes involved in the production of chemical defense reaction products, for example triptolides and/or derivatives thereof; and it provides the plant cells with terpene synthesis precursors.

The composition of the elicitation cocktail is, for example, as follows: 0.5-5 mg/l benzylaminopurine (BAP), for example 0.5-3 mg/l, for example 0.7-3 mg/l; 2-6 mg/l 5-chlorosalicylic acid (5-chloro SA), for example 3-5 mg/l, for example 3 mg/l or 5 mg/l; 20-60 mg/l acetylsalicylic acid (ASA) and/or salicylic acid, for example 30-50 mg/l, for example 33 mg/l or 45 mg/l; 22.4 mg/l methyl jasmonate (MeJA); 19-40 mg/l farnesol (F—OH); and 20-30 mg/l geraniol; wherein the quantity in mg/l corresponds to mg/l of culture medium. These are not the concentrations of the various products in a stock solution.

The elicitation cocktail is introduced into the culture medium using concentrated stock solutions prepared in dimethyl sulfoxide, for example.

The elicitation phase (iii) is carried out for 3-30 days, for example 10-30 days, for example 21-24 days.

Preferably, the elicitation phase (iii) is carried out in the dark. Preferably, the elicitation phase is carried out at roughly 27° C. Preferably, the elicitation phase is carried out with agitation.

According to a first laboratory-scale embodiment, the cells in suspension are cultured in containers of roughly 250 ml in volume, for example in Erlenmeyer flasks or culture bottles.

According to a second industrial-scale embodiment, the cells in suspension are cultured in a bioreactor with agitation and supplied with air enriched in pure oxygen. The culture device comprises, for example, two interconnected bioreactors. This is a binary culture device. One bioreactor can be a tank or bag bioreactor. The first bioreactor of the binary device is the propagation bioreactor. The second is the production bioreactor. The biomass can be transferred between the first reactor and the second reactor. Thus, the first reactor in which the propagation phase takes place feeds the second bioreactor with biomass for the production phase. With each transfer, the first propagation bioreactor preserves a portion of cell suspension to relaunch a propagation step with fresh propagation medium. This is the starter culture technique. The first bioreactor can be preceded by smaller bioreactors to supply the precultures required for industrial-scale production.

At the same time, the second production bioreactor, which receives the biomass from the first bioreactor, is supplemented optionally with nutrient medium for hormonal elimination or directly with production medium for the secondary metabolite. The elicitation cocktail is then introduced into the production bioreactor.

These two tank cultures are regulated in temperature, partial pressure of oxygen ($pO_2$) and partial pressure of carbon dioxide ($pCO_2$) in the following manner. Bioreactor temperature is maintained by temperature-controlled water circulating in a closed system within the bioreactor's walls.

An oxygen probe is calibrated in saturated air and provides data in real time to a computerized $pO_2$ regulator activated so as to maintain $pO_2$ at 80% by injecting sterile pure oxygen into the aeration system. This bioreactor is also equipped with a device for in-line measurement of $CO_2$ in effluent gases (head space) which provides data in real time to a computerized $pCO_2$ regulator so as to maintain $pCO_2$ at 6%. The latter is achieved by injecting sterile atmospheric air into the aeration system in mixture with oxygen. The bioreactor is also equipped with a stirring blade system turning at a constant speed sufficient to stir the cell suspension and to prevent it from forming sediment.

The inventive method is particularly advantageous since:
 culture productivity is greater than 2.75 mg of triptolide per liter per day,
 triptolide concentration in the culture supernatant after step (iii) is greater than 50 mg/l, and
 triptolide concentration in percent (w/w) of dry biomass is roughly 0.385%.

In comparison, document CN101358180A describes a volume productivity of 0.041 mg of triptolide per liter per day (0.82 mg/l in 20 days of culture). The method of the present invention produces in roughly 6.5 hours what the method of CN101358180 produces in several days.

Step (iv) of the method of the invention consists in extracting triptolide from the culture medium in which it is produced.

Triptolide can be extracted from the culture medium by methods well-known to those persons skilled in the art, for example by liquid/liquid extraction.

Said extraction leads either to pure triptolide or to a triptolide-enriched extract.

According to a particular embodiment of the invention, step (iv) is liquid/liquid extraction by isopropyl acetate.

Another object of the invention is a dedifferentiation medium such as described above.

Another object of the invention is the propagation medium for producing the biomass.

Another object of the invention is the hormonal elimination medium.

Another object of the invention is the elicitation cocktail as described above.

Another object of the invention is the use of the elicitation cocktail as described above for the cell culture of the species *Tripterygium*.

Another object of the invention relates to a triptolide-enriched extract that can be obtained by extraction from the culture medium of an in vitro culture of dedifferentiated cell of the species *Tripterygium*, in particular *Tripterygium wilfordii*. Preferentially, said triptolide-enriched extract can be obtained by the method for producing triptolide in culture medium from a cell culture of the species Tripterygium according to the invention.

Another object of the invention relates to a dermocosmetic or dermatological composition comprising triptolide or triptolide-enriched extract as active principle and one or more dermocosmetically and/or dermatologically acceptable excipients.

The dermocosmetically and/or dermatologically acceptable excipients can be any excipient among those known to those persons skilled in the art in order to obtain a composition for topical application in the form of a cream, lotion, gel, pomade, emulsion, microemulsion, spray, etc.

The dermocosmetic or dermatological composition of the invention can in particular contain additives and formulation aids such as emulsifiers, thickeners, gelling agents, water fixers, spreading agents, stabilizers, colorants, fragrances and preservatives.

Another object of the invention relates to a dermatological composition comprising triptolide or triptolide-enriched extract as active principle and one or more cosmetically and/or pharmaceutically acceptable excipients, to be used to treat cutaneous inflammatory disorders, preferentially pruritus, eczema, atopic dermatitis and psoriasis.

Another object of the invention relates to the use of a dermatological composition comprising triptolide or triptolide-enriched extract as active principle and one or more dermocosmetically and/or dermatologically acceptable excipients, to manufacture a drug intended to treat cutaneous inflammatory disorders, preferentially pruritus, eczema, atopic dermatitis and psoriasis.

Another object of the invention relates to a triptolide-enriched extract for use as a drug.

Another object of the invention relates to triptolide or triptolide-enriched extract for use to treat cutaneous inflammatory disorders, preferentially pruritus, eczema, atopic dermatitis and psoriasis.

Another object of the invention relates to the use of triptolide or triptolide-enriched extract to manufacture a drug to treat cutaneous inflammatory disorders, preferentially pruritus, eczema, atopic dermatitis and psoriasis.

Another object of the invention relates to the dermocosmetic use of triptolide or triptolide-enriched extract.

The following figures and examples illustrate the invention without limiting its scope.

FIG. 1: Example of bioreactor culture (binary system). Propagation of biomass in fermentor A, transfer of the medium to production fermentor B, elimination, elicitation and biomass harvesting after a few weeks.

Figure 2:
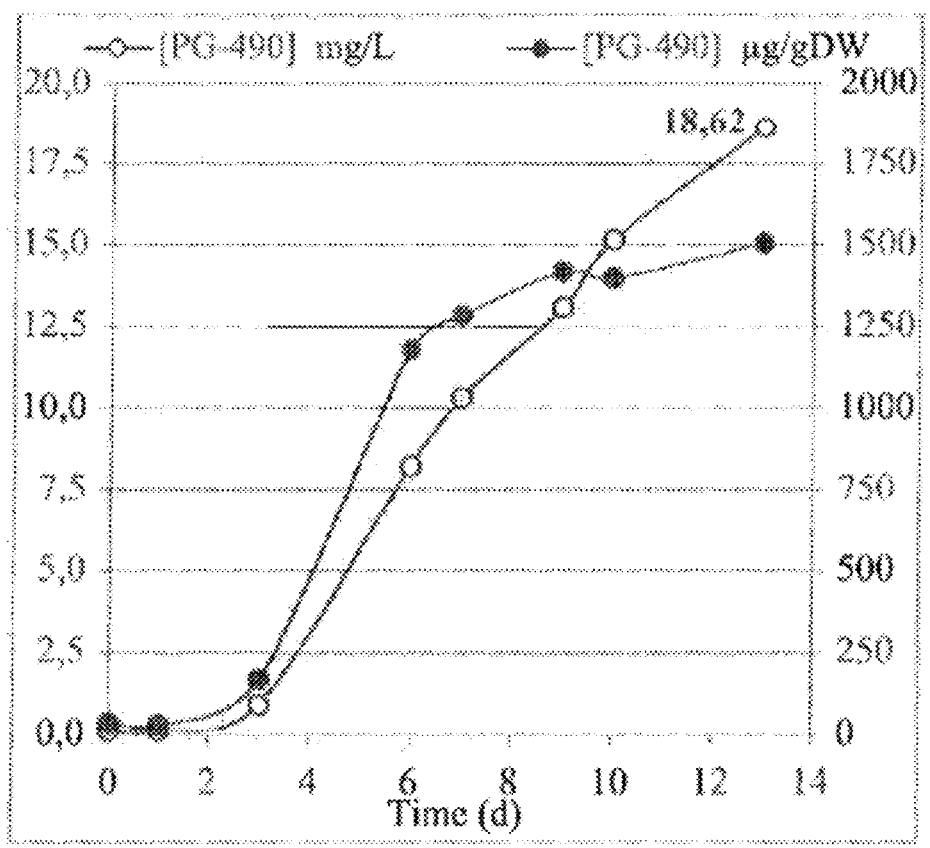

FIG. 2: Example of the kinetics of triptolide (PG 490) production by elicitation in fermentor B.

Figure 3:
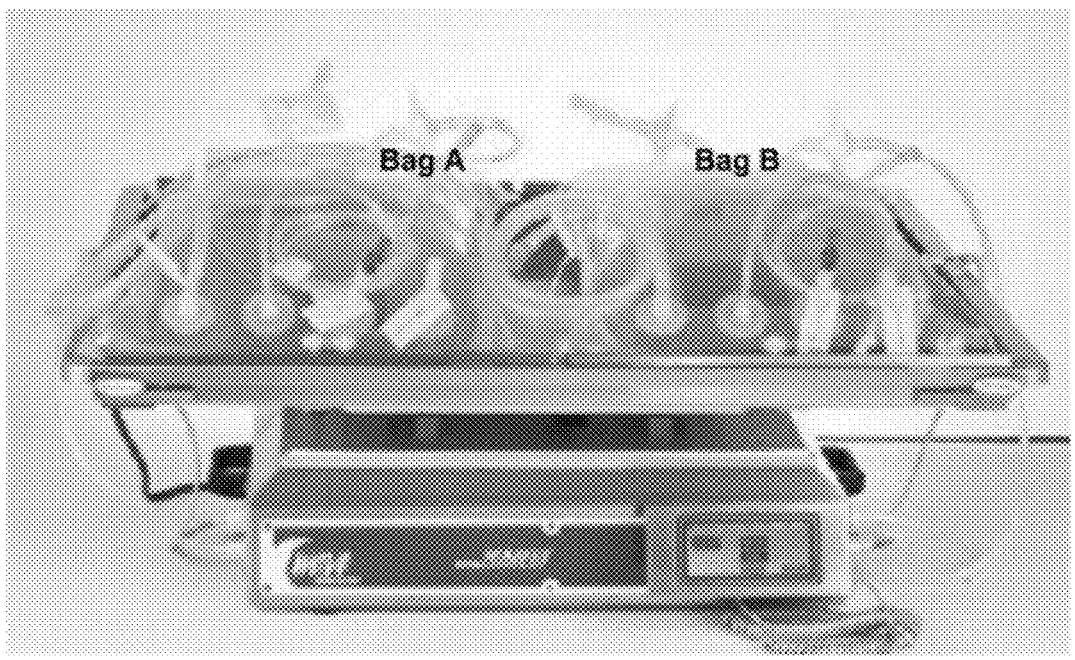

FIG. 3: Disposable WAVE 20/50EHT (GE Healthcare Biosciences) rocker bioreactor equipped with an air/pure oxygen mixing controller (O2MIX), a dissolved oxygen partial pressure ($pO_2$) measurement system (DOOPT20 +DOOPT-PROBE) and a heating plate (regulating the temperature at 27° C.) for installing 10- and 20-liter Cellbags (20EHT kit).

Figure 4:
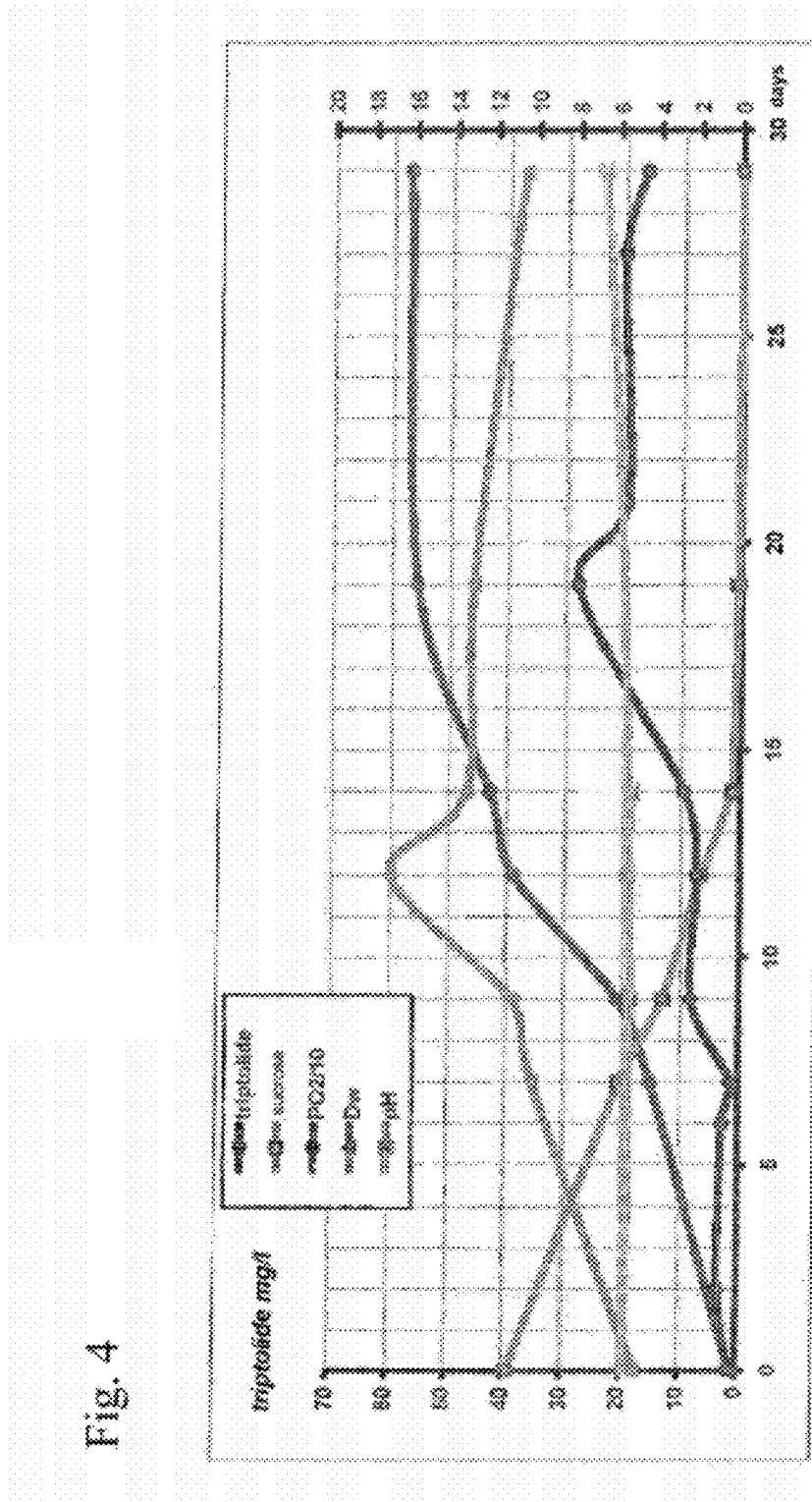

FIG. 4: Kinetics of the triptolide production culture in a WAVE disposable bioreactor. Follow-up of physicochemical parameters: pH, partial pressure of dissolved oxygen ($pO_2$), sucrose consumption, evolution in dry biomass (DW) and triptolide concentration in the culture supernatant.

Figure 5:
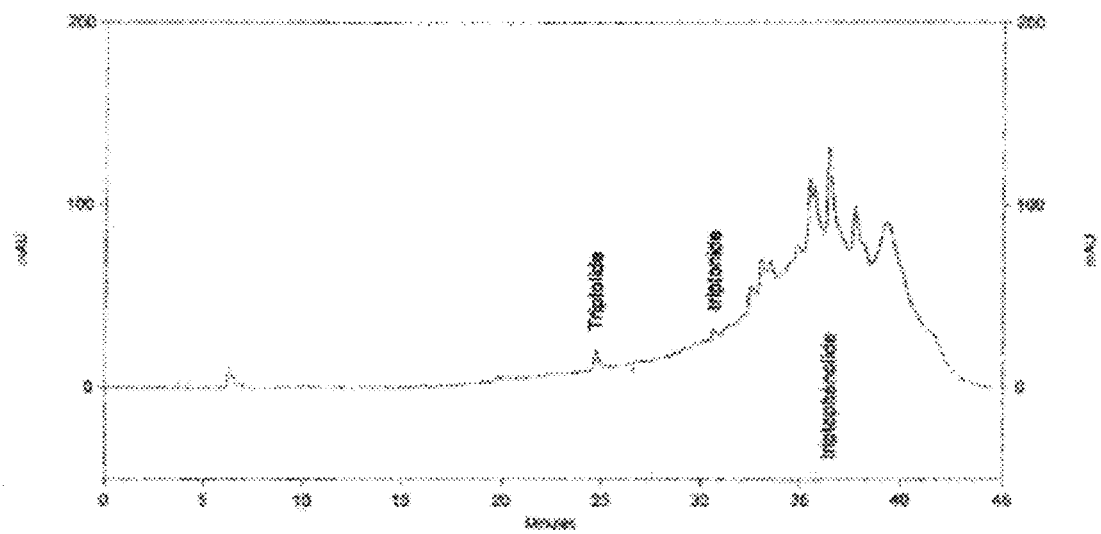
Figure 5:
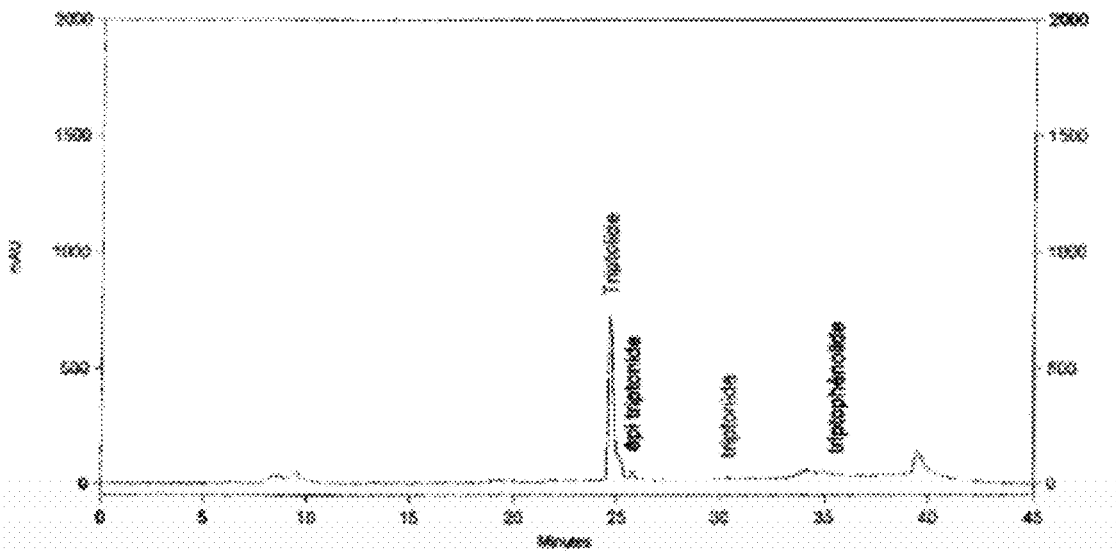

FIG. 5: HPLC assay to determine triptolide concentration in the extract.

Figure 6:
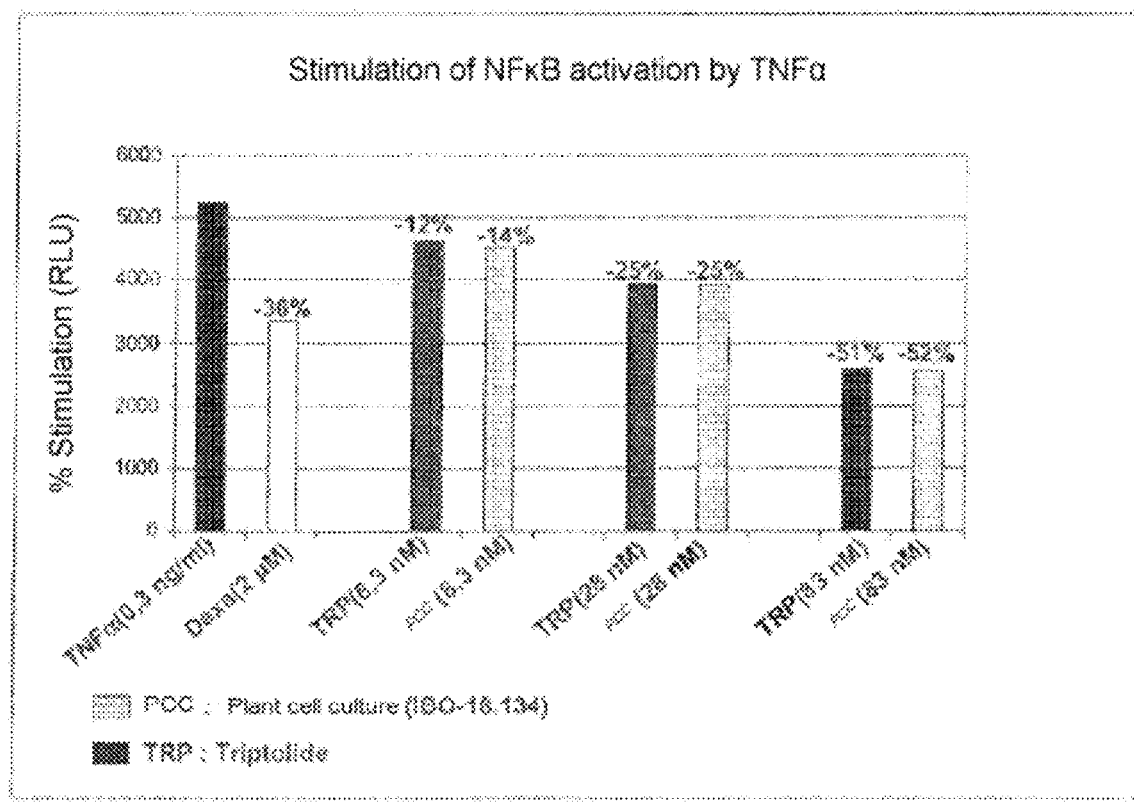

FIG. 6: Test of NFκB inhibition by PCC extract.

Figure 7:
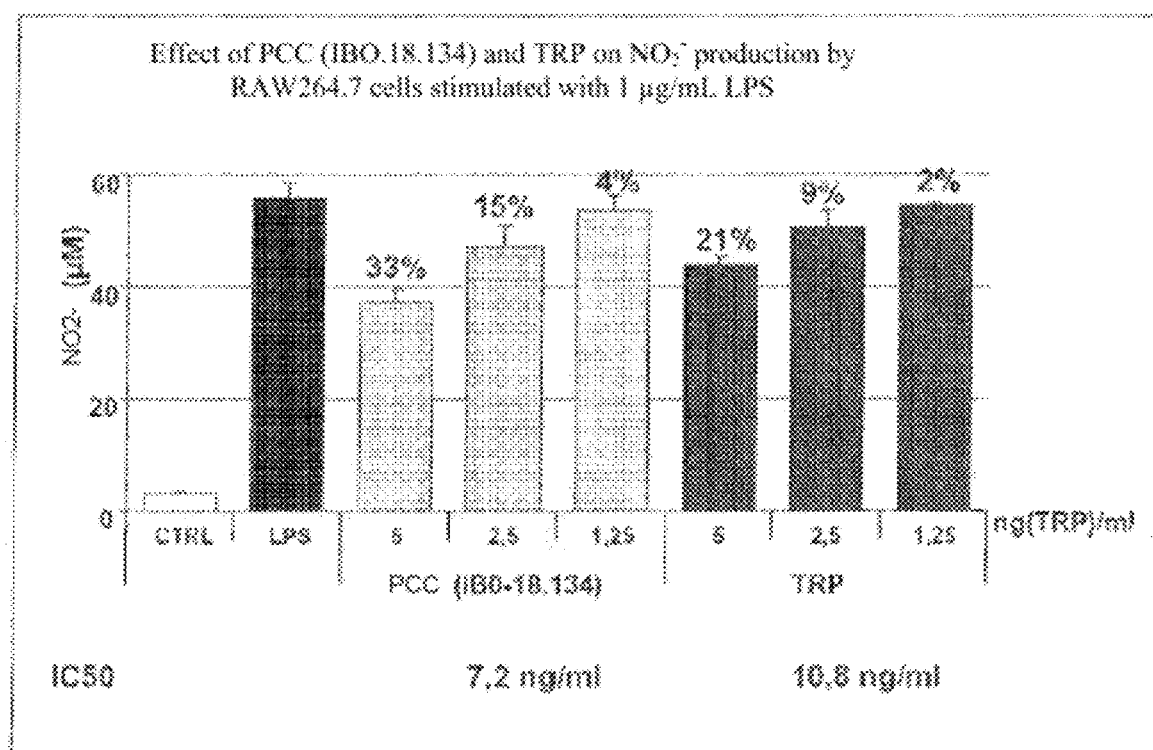

FIG. 7: Effect of PCC extract (IBO.18.134) on $NO_2^-$ production by RAW264.7 cells stimulated with 1 μg/ml of LPS.

Figure 8:
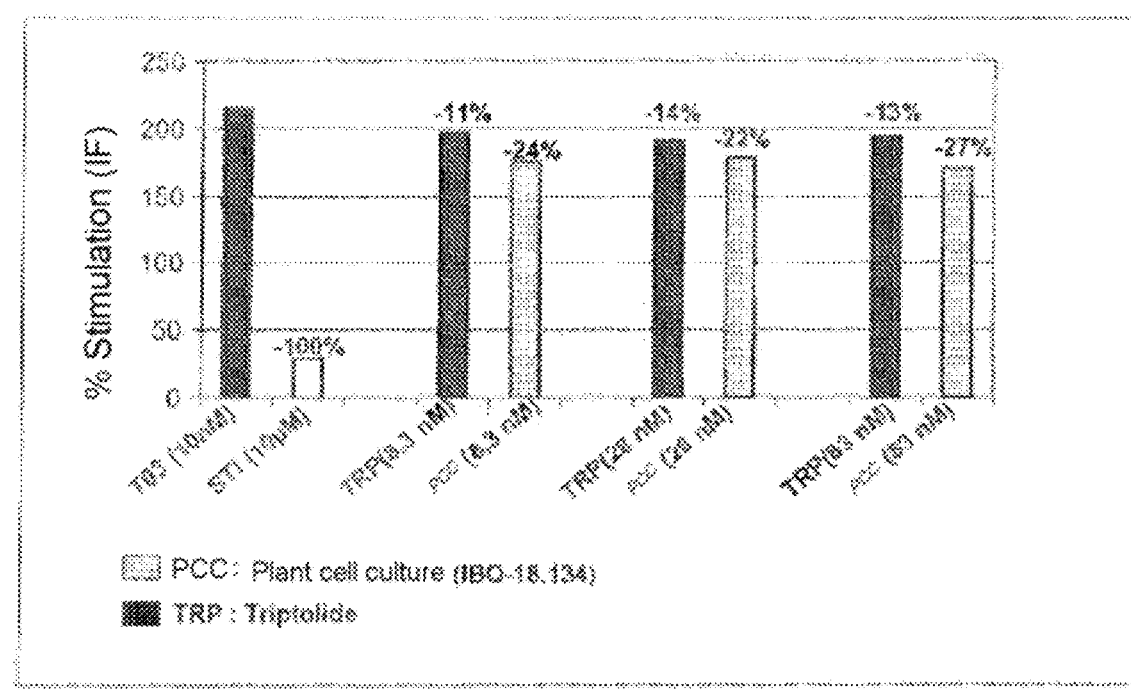

FIG. 8: Effect of PCC extract on PAR-2 inhibition.

Figure 9:
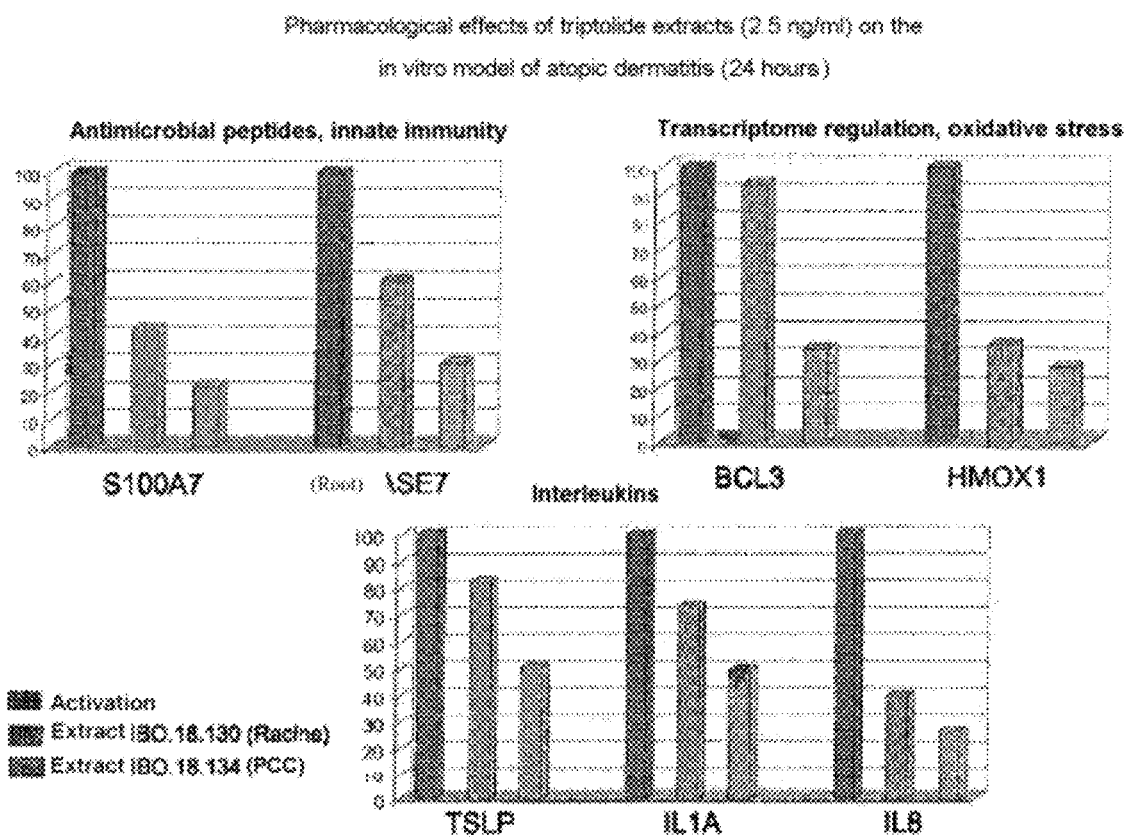

FIG. 9: Effect of compounds on the atopic dermatitis model.

Figure 10:
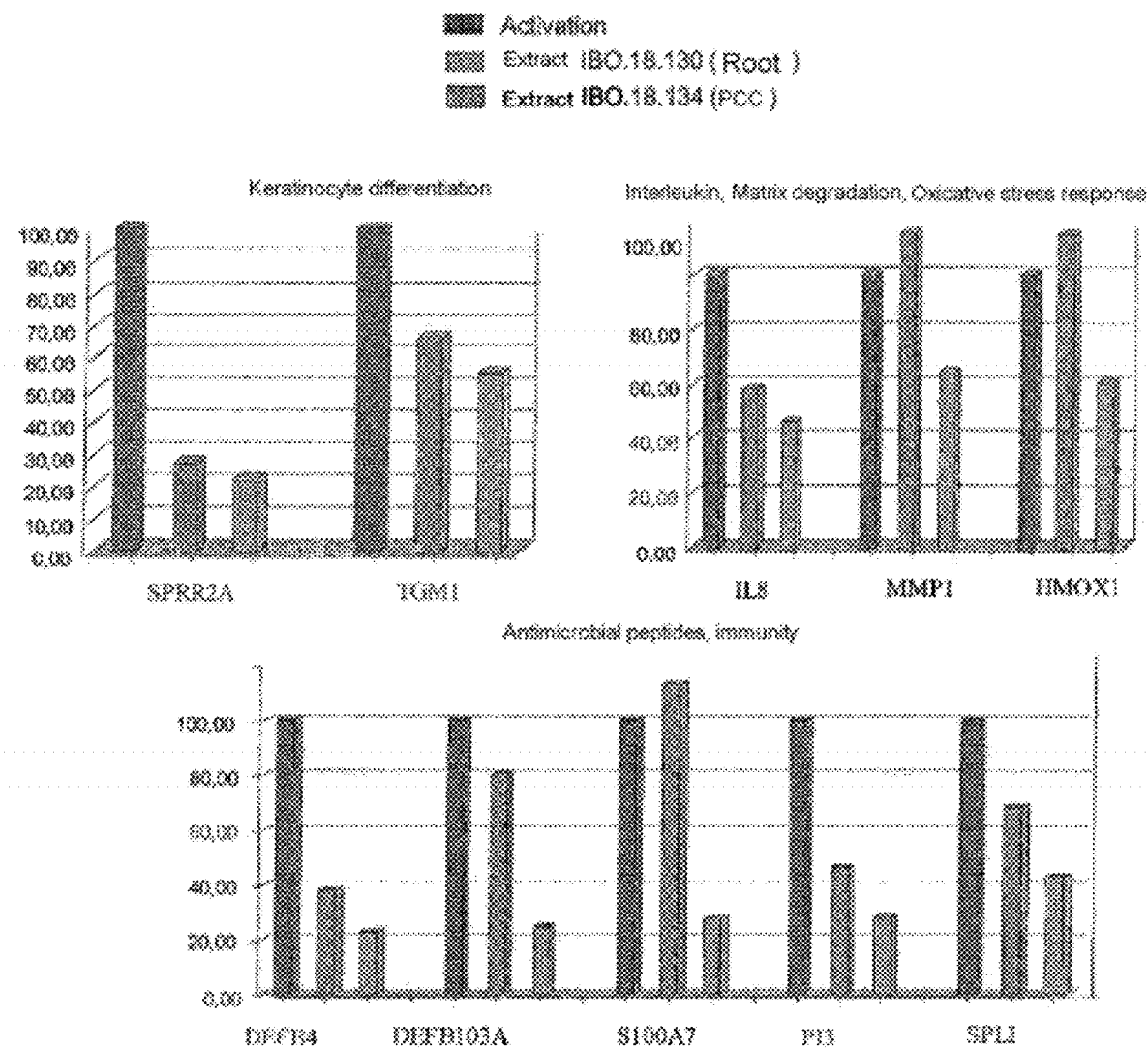

FIG. 10: Effect of compounds on the psoriasis model.

Figure 11:
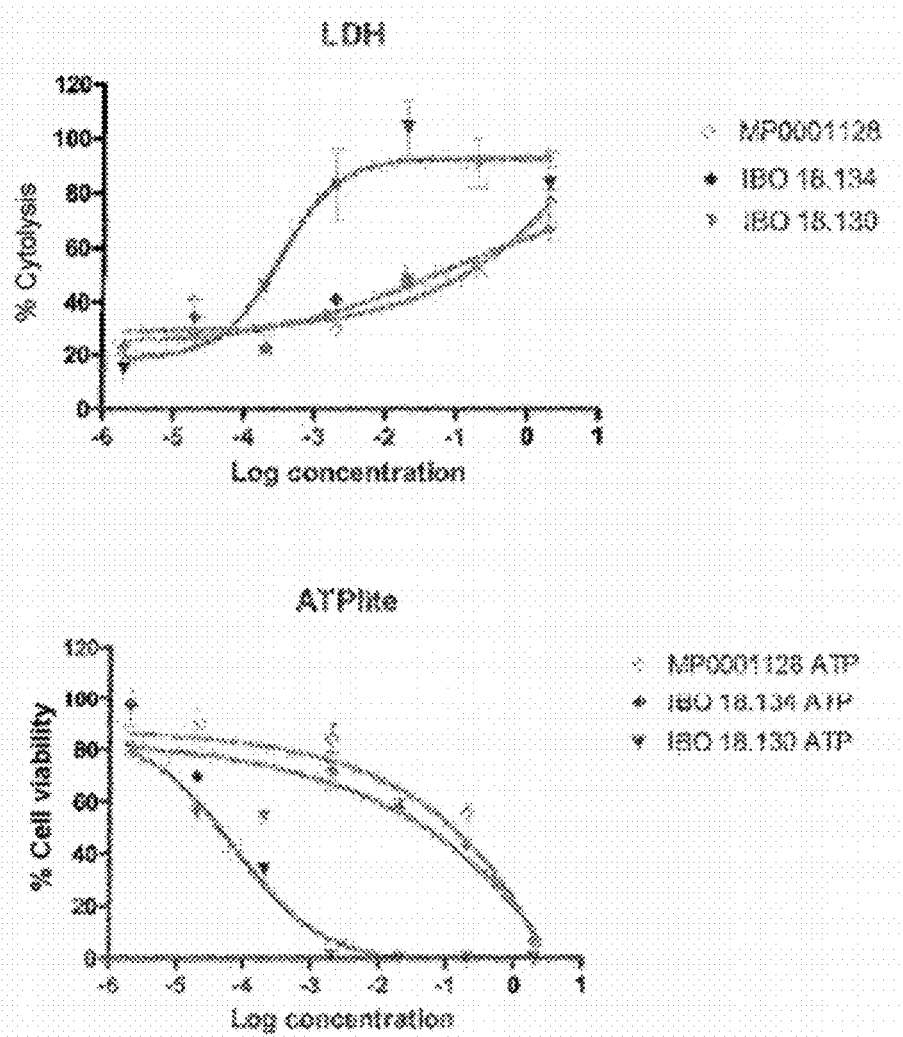

FIG. 11: Cytotoxicity tests (ATPlite and LDH assays).

EXAMPLE 1

Cell Dedifferentiation Protocol

Calluses are obtained from *Tripterygium wilfordii* leaf explants.

The explants are sterilized with 70% ethanol followed by sodium hypochlorite containing 2.5% active chlorine, and then rinsed with sterile demineralized water. Optionally, the explants are washed with 7% hydrogen peroxide before being rinsed with sterile demineralized water.

The leaves are cut into pieces, for example into squares roughly 8-10 mm on each side. The foliar explants are deposited on agar medium for dedifferentiation induction (MSO medium) and reinoculation.

The composition of the dedifferentiation medium is as follows:

Macroelements: 1650 mg/l $NH_4NO_3$; 1900 mg/l $KNO_3$; 440 mg/l $CaCl_2.2H_2O$; 370 mg/l $MgSO_4.7H_2O$; 170 mg/l $KH_2PO_4$;

Microelements: 0.83 mg/l KI; 6.2 mg/l $H_3BO_3$; 22.3 mg/l $MnSO_4.4H_2O$; 6.61 mg/l or 8.6 mg/l $ZnSO_4.H_2O$; 0.25 mg/l $Na_2MoO_4.2H_2O$; 0.025 mg/l $CuSO_4.5H_2O$; 0.025 mg/l $CoCl_2.6H_2O$; 27.8 mg/l $FeSO_4.7H_2O$; 37.3 mg/l $Na_2EDTA.2H_2O$;

Vitamins: 100 mg/l myo-inositol; 0.5 mg/l nicotinic acid; 0.5 mg/l pyridoxine-HCl; 0.5 mg/l thiamine-HCl; 2 g/l glycine;

Carbon source: 30 g/l sucrose;

Hormones: 0.1 mg/l kinetin; 0.5 mg/l 2,4-dichlorophenoxyacetic acid (2,4-D); 1 mg/l naphthalene acetic acid (NAA).

The dedifferentiation medium is gelled by adding agar at a concentration of 8-12 g/l, and its pH is adjusted to 6±0.5 before autoclaving for 20 min at 121° C. Petri dishes containing the explants are incubated in the dark at 27-28° C.

The calluses obtained are detached from the foliar explants and deposited on new dedifferentiation agar. The calluses are reinoculated every month on the same agar medium.

EXAMPLE 2

Formulation of the Propagation and Culture Media

After friable calluses are obtained, after a few months of reinoculation, they are transferred to liquid culture medium, optimized for the propagation of the cell suspension.

The cell suspension is prepared by depositing roughly 40 g of friable calluses in a 200 ml Erlenmeyer flask containing the propagation medium and incubating for one week on an agitation mixer set at 100 rpm in the dark at 27-28° C. The cell supernatant is collected with a pipette leaving residual callus clusters. The cell suspension obtained is cultured for 15 days and then propagated by ⅕ dilution in new medium every 15 days. The cell suspensions cultured on propagation media TW2H6 gave rise to the NS line.

The propagation medium has, for example, the composition indicated below:

Macroelements: 1650 mg/l $NH_4NO_3$; 2500 mg/l $KNO_3$; 440 mg/l $CaCl_2.2H_2O$; 370 mg/l $MgSO_4.7H_2O$; 130 mg/l $KH_2PO_4$;

Microelements: 0.41 mg/l KI; 6.2 mg/l $H_3BO_3$; 22.3 mg/l $MnSO_4.4H_2O$; 7.5 mg/l $ZnSO_4.H_2O$; 0.25 mg/l $Na_2MoO_4.2H_2O$; 0.025 mg/l $CuSO_4.5H_2O$; 0.025 mg/l $CoCl_2.6H_2O$; 19.85 mg/l $FeSO_4.7H_2O$; 26.64 mg/l $Na_2EDTA.2H_2O$;

Vitamins: 50 mg/l myo-inositol; 0.25 mg/l nicotinic acid; 0.25 mg/l pyridoxine-HCl; 0.25 mg/l thiamine-HCl;

Hormones: 0.083 mg/l kinetin; 0.575 mg/l 2-4 dichlorophenoxyacetic acid (24-D); 0.350 mg/l naphthalene acetic acid (NAA);

Carbon source: 30 g/l sucrose.

The pH of the medium is adjusted to 6±0.5 before a suitable sterilization treatment, for example autoclaving at 121° C. for at least 20 minutes or sterile filtration at 0.2 μm.

The Erlenmeyer flasks are filled to 20-40% capacity and the inoculum per cell suspension transfer is 20-25% of the volume, i.e. roughly 50-100 g/l of fresh biomass. The culture thus proceeds for 15 days in the dark at 27-28° C. with orbital agitation at 110-120 rpm (rotation per minute). At this stage the biomass is present at a concentration of up to roughly 320-350 g/l of fresh biomass.

The propagation can also take place in dedifferentiation medium.

EXAMPLE 3

Triptolide Production in Erlenmeyer Flasks

Production in Erlenmeyer flasks is divided into three phases:
1. Cell culture on propagation medium for 15 days.
2. Hormonal elimination for 7 days.
3. Triptolide production via elicitation for roughly 20 days.

At the end of a 15-day propagation culture of the biomass in Erlenmeyer flasks, as indicated above, it is allowed to sediment so as to make it possible to partially withdraw the supernatant, for example ⅓ of the total volume of the suspension, and to replace it with the same volume of hormonal elimination medium, for example the hormonal elimination medium described below. The objective of this elimination medium is to eliminate residues of growth hormone 2,4-D, which is a triptolide production inhibitor, present in the propagation medium. The composition of the hormonal elimination medium is as follows:

Macroelements: 2 g/l $NH_4NO_3$; 3 g/l $KNO_3$; 440 mg/l $CaCl_2.2H_2O$; 370 mg/l $MgSO_4.7H_2O$; 43 mg/l $KH_2PO_4$; 2 g/l sodium pyruvate;

Microelements: 0.41 mg/l KI; 6.2 mg/l $H_3BO_3$; 22.3 mg/l $MnSO_4.4H_2O$; 7.5 mg/l $ZnSO_4.H_2O$; 0.25 mg/l $Na_2MoO_4.2H_2O$; 0.025 mg/l $CuSO_4.5H_2O$; 0.025 mg/l $CoCl_2.6H_2O$; 19.85 mg/l $FeSO_4.7H_2O$; 26.64 mg/l $Na_2EDTA.2H_2O$;

Vitamins: 50 mg/l myo-inositol; 0.25 mg/l nicotinic acid; 0.25 mg/l pyridoxine-HCl; 0.25 mg/l thiamine-HCl; 1 g/l glycine;

Hormones: 1.1 mg/l kinetin; 2 mg/l indole-butyric acid (IBA);

Carbon source: 30 g/l sucrose. The pH is adjusted to 6±0.5 before autoclaving for 20 min at 121° C.

Elimination is carried out in this manner for 7 days in the dark at 27-28° C. with orbital agitation at 110-120 rpm.

Once the elimination step is carried out, the biomass is dried using a Buchner filtration apparatus and inoculated in new hormonal elimination medium at a concentration of roughly 100-200 g/l of fresh biomass.

The elicitation cocktail is introduced, for example using stock solutions prepared in dimethylsulfoxide, into the culture medium. The composition of the cocktail elicitor is as follows: 1.25 mg/l abscisic acid (ABA); 0.7 mg/l or 3 mg/l benzylaminopurine (BAP); 3 mg/l or 5 mg/l 5-chlorosalicylic acid (5-chloro SA); 33 mg/l or 45 mg/l acetylsalicylic acid (ASA); 22.4 mg/l methyl jasmonate (MeJA); 19 mg/l or 30 mg/l farnesol (F—OH); and 23 mg/l geraniol.

Triptolide production is carried out in this manner for 10-21 days in the dark at 27-28° C. with orbital agitation at 120 rpm. When culturing stops, the medium is filtered to recover the clear, dark-colored supernatant which contains the majority of triptolide.

The triptolide concentration in the culture supernatant is 50-70 mg/l, for example 45-65 mg/l of culture medium.

EXAMPLE 4

Triptolide Production in Stirred-Tank Bioreactors

Triptolide production in bioreactors is divided into three phases:
1. Cell culture on propagation medium for 15 days.
2. Hormonal elimination for 7 days.
3. Triptolide production via elicitation for 21 days.

Cell culture and propagation on propagation medium:

At the end of a 15-day propagation culture of the biomass in Erlenmeyer flasks, as indicated above, it is used as inoculum for culturing in a 10 l bioreactor (reactor A). See the binary system of FIG. 1.

The 2 l inoculum is poured into the propagation bioreactor (A). This bioreactor contains 8 l of propagation medium at 27.5° C.

An oxygen probe is calibrated in saturated air and provides data in real time to a computerized $pO_2$ regulator activated so as to maintain $pO_2$ at 50-80%. This bioreactor is also equipped with a device for in-line measurement of $CO_2$ in effluent gases (head space) which provides data in real time to a computerized $pCO_2$ regulator so as to maintain $pCO_2$ at 6-8%. The bioreactor is also equipped with a stirring blade system turning at 75 rpm so as to avoid sedimentation of the cells at the bottom of the reactor.

The culture is maintained under these physicochemical conditions for 15 days so as to reach a cellular density of the order of 320 g/l of fresh biomass.

Next, this bioreactor is connected in a sterile manner to another bioreactor called the production bioreactor (B). The equivalent of 1700 g fresh biomass (roughly 5.3 l of volume) is transferred from A to B.

Propagation bioreactor A keeps a remainder of 2 l of suspension to which is added a volume of 8 l of propagation medium poured in such a way as to restart cell propagation.

Elimination and production on elimination medium:

At the same time, production bioreactor B is supplemented with elimination medium so as to reach a volume of 10 l and a cell density of 170 g/l. The culture in the production bioreactor is maintained in this state for 4-6 days so as to completely separate the biomass from traces of growth hormones, namely auxins such as 2,4-D, present in the propagation medium. The elicitation cocktail is then introduced into production bioreactor B. Triptolide production is carried out in this manner for 15-21 days. FIG. 2 shows an example of the kinetics follow-up of triptolide production after elicitation (at t=0) in tank B. At the end of the culture, the culture supernatant is recovered by a prefiltration step (15-20 μm) followed by filtration at 0.2 μm. A clear solution is obtained. The triptolide concentration obtained is 20-35 mg/l in the extracellular medium.

This type of binary culture can be scaled up to larger fermentors (greater than 100 l in volume).

EXAMPLE 5

Triptolide Production in WAVE Disposable Bag Bioreactors

Another method advantageously using very simple and inexpensive equipment makes it possible to have a yield comparable to the system described above, namely disposable reactors that do not require extensive maintenance and cleaning as in the case of traditional stainless-steel fermentors. The stirred reactor is commonly used in the culture of suspended mammalian cells. The illustrated example is described for WAVE reactors, for example, sold by GE Healthcare Biosciences, for volumes of 10 l or 20 l, but the method can be adapted and applied to larger volumes and to equipment from other manufacturers.

The binary system described above for traditional glass laboratory bioreactors or stainless-steel industrial reactors is applied in the same manner with two WAVE bags. See illustrations in FIG. 3.

Propagation:

WAVE bioreactor A (10 l) placed on its support is filled with nutrient medium by in-line sterile filtration and inflated with air. It is then inoculated with pre-culture prepared in an Erlenmeyer flask agitated for 15 days in propagation medium, in an agitating incubator.

The bioreactor is incubated according to the following conditions:

rocking angle: 6-8° rocking speed: 16-20 rpm aeration rate: 0.1-0.15 l/min of air enriched with 50% pure oxygen

T=27° C.

duration=14 days

Elicitation and Production:

A volume of roughly 500 ml of culture from bag A is transferred to bag B (10 l) placed beside bag A on the tray. The remainder of bag A (roughly 2 l) is diluted with 2 l of 2× elimination medium. Agitation continues at T=27° C. The culture in elicitation phase is monitored by measuring certain parameters (see FIG. 4). The maximum triptolide concentration is 55 mg per liter of culture supernatant, after 19 days of incubation. The triptolide production rate is roughly 2.87 mg/l of acellular supernatant per day of culture. The triptolide production kinetics start to dip just after the consumption of almost all the available sucrose. At the end of the culture, the culture supernatant is recovered followed by a prefiltration step (15-20 μm) and a second filtration step at 0.2 μm. A clear, colored (yellow or mauve-pink) solution is obtained.

EXAMPLE 6

Triptolide Production in a WAVE Bioreactor

Incubation temperature: +27° C. for all phases (cell multiplication and elicitation in flasks and bioreactor).

Preculture:

A preculture is prepared in an agitated 1-liter flask containing 400 ml of propagation medium TW2H6, which was inoculated with 100 ml of a roughly 15-day culture.

TABLE 1

Characteristics of the final preculture

| t0 + 15 d | Container | NS culture | pH | Fw (g/l) | Dw (g/l) | Sucrose (g/l) | Triptolide (mg/l) |
|---|---|---|---|---|---|---|---|
| NSP6G | 1 liter Erlenmeyer | Beige | 5.6 | 131 | 7.2 | 10.4 | 2.9 |

Culture in the WAVE Bioreactor:

500 ml of inoculum is transferred, via a sterile connection, to the disposable bioreactor set-up and filled with sterile nutrient medium. It is incubated on the rocker according to following conditions:
- rocking angle: 6-8°
- rocking speed: 16-18 rpm
- aeration rate: 0.1-0.15 l/min of air with enriched 50% pure oxygen
- culture duration: roughly 14 days

TABLE 2

Characteristics of the final culture

| t0 + 14 d | Container | NS culture | pH | Fw (g/l) | Dw (g/l) | Sucrose (g/l) | Triptolide (mg/l) |
|---|---|---|---|---|---|---|---|
| EW4-NSP7 | 10 liter bag | Light khaki beige | 5.8 | 253 | 9.7 | 0.5 | 1.1 |

Elicitation in the WAVE Bioreactor:

A volume of 2 liters of this culture is elicited by dilution in 2 liters of elimination medium containing 2× concentrated elicitation cocktail, and incubation continues under the following conditions:
- rocking angle: 6-7°
- rocking speed: 17-21 rpm
- aeration rate: 0.1-0.15 l/min of air enriched with 50% oxygen Results:

Cell multiplication and metabolite production via elicitation were carried out in disposable bioreactors, for example WAVE bags.

The progression of the culture in elicitation phase is represented in FIG. 4.

During the elicitation phase, certain parameters are monitored:

The dry mass in suspension (DW): it increases from 5 to 13 g/l in 10 days, stagnates for 10 days, then slightly decreases to 10 g/l in 10 days, probably due to the start of cell lysis.

pH is rather stable for 20 days (around 5.5), then gradually increases to 7 over the last 10 days of culture. This rise in pH could be attributed to cell lysis and the release of the cytoplasmic contents.

Partial pressure of oxygen ($pO_2$; percentage of oxygen saturation of the medium) reflects the quantity of oxygen dissolved in the medium at the time of measurement, therefore the resultant between the total quantity the medium can contain (saturation) and the quantity of oxygen consumed by the cells.

Total sucrose concentration decreases during the first 15 days at a rate of 2.7 g/l per day.

Triptolide concentration increases to about 55-56 mg/l in 19 days, and then remains practically stable until the end of culture.

EXAMPLE 7

Production of Triptolide-Enriched Extract IBO.18.134 by Liquid/Liquid Extraction of *Tripterygium wilfordii* Culture Supernatant Roughly 30 l of culture supernatant containing the triptolide obtained in example 6 is extracted with one volume of isopropyl acetate (twice in succession). The organic phases are concentrated and dried in a rotary evaporator. 650 mg of beige-yellow dry matter is obtained. An HPLC assay is used to determine the triptolide concentration in the extract: 195 mg of triptolide contained in 0.65 g of recovered powder, or 0.3 g of triptolide per gram of dry extract. (See FIG. 5.)

EXAMPLE 8

(Comparative Example): Production of Triptolide-Enriched Extract IBO.18.130 from Roots

*Tripterygium wilfordii* roots are barked, dried and ground. They are then extracted with 90% ethanol. Once concentrated, the extract undergoes liquid/liquid extraction with 1,2-dichloroethane. The chlorinated phase is washed with basic solution (NaOH), concentrated and adsorbed on silica. This crude extract on silica is stored at −20° C.

The *Tripterygium wilfordii* roots adsorbed on silica are extracted with methanol as follows: 200 g of crude extract on silica in 1 liter of methanol (a single extraction) is left under magnetic stirring at room temperature for 1 hour. The methanol phase is then dried in a rotary evaporator. 25 g of brown-orange dry matter is obtained. An HPLC assay is used to determine the triptolide concentration in the extract: 90 mg of triptolide is contained in 25 g of recovered powder, or 0.0036 g of triptolide per gram of dry extract. (See FIG. 5.)

The following examples 9 to 12 compare:

1) Plant cell culture (PCC) extracts of example 7 compared to pure triptolide (with identical triptolide (TRP) concentrations):
- inhibition of NFκB transcription (inhibition of proinflammatory and inflammatory responses),
- inhibition of nitrite ($NO_2$) production,
- PAR-2 inhibition.

2) The root (R) extracts of example 8 and plant cell culture (PCC) extracts of example 7 in terms of pharmacological activities (at identical TRP concentrations):
- inhibition of inflammatory genes (atopic dermatitis model),
- inhibition of inflammatory genes (psoriasis model).

3) In vitro cytotoxicity of the two extracts R and PCC was also compared.

EXAMPLE 9

Test of NFκB Inhibition by PCC Extract

Transcription factor NFκB controls the expression of a large number of genes involved in inflammatory response regulation. Certain proinflammatory stimuli, such as tumor necrosis factor-α (TNFα), lead to NFκB activation, i.e., to its nuclear translocation. Consequently, NFκB will induce the transcription of proinflammatory genes coding for cytokines, chemokines, adhesion molecules, growth factors and inducible enzymes such as cyclooxygenase-2 (COX-2) and nitric oxide synthase (iNOS). NFκB plays a key role in the initiation and amplification of the inflammatory response. Certain chronic inflammatory diseases of the skin, such as atopic dermatitis or psoriasis, are characterized by deregulation of the expression of inflammation mediators expressed by keratinocytes. The anti-inflammatory activity of pure triptolide (TRP) in relation to that of plant cell culture extracts (IBO.18.134) with equivalent amounts of TRP is evaluated.

Results:

FIG. 6 represents the inhibition of various extracts on NFκB activation following TNFα stimulation in HaCaT keratinocyte cells. As a positive control, dexamethasone (2 μM), which inhibits NFκB activation by 36%, was used. Pure triptolide inhibits in a dose-dependent manner from 8 nM to 83 nM.

At identical triptolide concentrations of 8 nM, 28 nM and 83 nM, NFκB inhibition by PCC and TRP are equivalent.

EXAMPLE 10

Effect of PCC Extract (IBO.18.134) on $NO_2^-$ Production by RAW264.7 Cells Stimulated with 1 μg/ml of LPS The objective of this study was to compare the anti-inflammatory activity of PCC extract (IB-134) with that of pure triptolide.

To this end, the test selected was $NO_2^-$ production by RAW264.7 cells stimulated with lipopolysaccharides (LPS).

Briefly, RAW264.7 cells (murine macrophages) were seeded at $1.4 \cdot 10^5$ cells/cm$^2$. After 24 hours, the cells were incubated for 1 hour with various concentrations of the products to be tested and then stimulated for 24 hours with 1 μg/ml of LPS. $NO_2$ concentration was estimated in the culture supernatants using the Griess reagent.

The results (FIG. 7) illustrate $NO_2^-$ production obtained under the various conditions specified above. The percent inhibition calculated in relation to the LPS control appears in each histogram. Lastly, IC$_{50}$ was calculated from these values (in bold blue).

The data obtained show that, under the conditions tested with identical TRP concentrations, the PCC extract (IBO.18.134) and TRP inhibit nitrite production induced by LPS, with inhibition slightly higher by PCC.

Comparison of IC$_{50}$ values shows that PCC is greater than TRP. PCC extract is revealed to be more active than pure triptolide in terms of $NO_2^-$ inhibition. (See FIG. 7.)

EXAMPLE 11

Effect of PCC Extract on PAR-2 Inhibition

Protease-activated receptor-2 (PAR-2) is associated with the physiopathology of several diseases involving inflammatory responses.

PAR-2 belongs to the superfamily of G-protein-coupled 7-transmembrane domain receptors, but has a single activation pathway.

Indeed, PAR2 is activated by serine proteases such as trypsin, tryptase and factors Xa and VIIa. Cleavage by these proteases of the extracellular portion of the receptor exposes a new amino-terminal domain (SLIGKV) which acts as a ligand "attached" to the receptor: it binds upon itself at extracellular loop 2 and undergoes autoactivation.

PAR-2 is expressed by the various cell types of the skin: keratinocytes, myoepithelial cells of the sweat glands, hair follicles, dendritic-like cells of the dermis and endothelial cells of the lamina propria and of the dermis. Melanocytes do not express this receptor although PAR-2 plays an important role in pigmentation by promoting the transfer of melanin from melanocytes to keratinocytes.

Serine proteases generated by the epidermis have chemotactic effects that induce leukocyte recruitment in the skin. They are also involved in the regulation of homeostasis, mitogenesis and epidermal differentiation and they modulate the barrier function of the skin. Moreover, serine proteases contribute to the physiopathology of cutaneous diseases related to inflammation, host defense, carcinogenesis, fibrosis and nerve stimulation.

The physiological and physiopathological cutaneous properties of serine proteases are in part related to PARs. Indeed, PAR-2 is overexpressed in the epidermis, dermis and vessels in inflammatory diseases of the skin such as atopic dermatitis, lichen planus and psoriasis. PAR-2 also plays a role in the development of pruritus in patients suffering from atopic dermatitis.

Activation of PAR-2 by a trypsin-type protease induces the production of IL8 from keratinocytes (HaCaT). More recently, it was shown that IL8, a chemokine that is chemoattractive for leukocytes, enables the infiltration of neutrophils into the epidermis of patients with psoriasis vulgaris.

Intracellular PAR-2 signaling is underpinned to some extent by mobilization of intracellular calcium.

It is thus proposed to evaluate the anti-PAR-2 activity of PCC extract (IBO.18.134) and triptolide on human keratinocytes from a cell line (HaCaT) by measuring the influx of intracellular calcium induced following the specific stimulation of PAR-2 by trypsin.

In vitro, on a cellular scale, stimulation of PAR-2 by trypsin leads to mobilization of intracellular calcium, which can be detected using a fluorescent probe.

It is noted that at an identical triptolide concentration, PAR-2 inhibition moderates both products tested, although inhibition is more marked by PCC at the concentrations tested. (See FIG. 8.)

EXAMPLE 12

Evaluation in the Atopic Dermatitis Model and the Psoriasis Model

The anti-inflammatory and soothing activity of triptolide obtained from root extract (IBO.18.130) is compared to that of PCC extract (IBO.18.134).

This evaluation was investigated in the context of the induction of an atopic dermatitis phenotype and a psoriasis phenotype in normal human epidermal keratinocytes. More particularly, the effect of these compounds was analyzed by PCR array (RNA chips) on the expression of two panels of 32 genes (mRNA) selected for their importance in the inflammation of keratinocytes and more precisely for their involvement in atopic dermatitis or psoriasis.

The effect of these compounds was studied in:
- keratinocytes exhibiting an atopic dermatitis phenotype after stimulation by poly(I:C) plus a combination of Th1 cytokines (TNFα) and Th2 cytokines (IL4+IL13), and
- keratinocytes exhibiting a psoriasis phenotype after stimulation by a combination of cytokines (IL17+OSM+ TNFα).

Material and Methods

1. Extracts

The extracts were solubilized in DMSO to prepare a 200 mg/ml stock solution expressed in concentration of pure triptolide. This concentration is imposed by the solubility of the root extract, which requires particular attention (dissolution at room temperature with gentle stirring).

The compounds were solubilized extemporaneously for the pharmacological tests, which were carried out for both extracts with 2.5 ng/ml of pure triptolide concentration equivalent.

2. Cell Type

The cells used are normal human epidermal keratinocytes (NHEK), which are amplified under standard culture conditions.

3. Pharmacology 3.1 Methodology

NHEK cells are seeded and cultured in keratinocyte-SFM culture medium. The culture medium is replaced with medium containing or lacking (control) the extracts being tested. After preincubating the inflammation inducer mixture for 1 hour, the mixture containing poly(I:C), IL4, IL13 and TNF, in the case of atopic dermatitis, is added; in the case of psoriasis, the mixture containing IL17, oncostatin M and TNF is added.

A control with no inducer or compound is also prepared in parallel, making it possible to validate the induced model (NHEK vs. NHEK±inducers).

All the conditions were carried out in duplicate.

RNA is extracted from the cells after incubating for 24 hours with the mixture of inducer±extracts with 2.5 ng/ml of pure triptolide equivalent.

3.2 Analysis of Differential Expression by RT-qPCR

After extraction of total RNA and synthesis of cDNA, 32 specific atopic dermatitis genes and 32 specific psoriasis genes are analyzed with quantitative PCR.

Quantified Genes

The lists of quantified genes characteristic of an atopic dermatitis phenotype and a psoriasis phenotype are presented in tables 1 and 2, respectively.

Results

1. Effects of Compounds on Keratinocytes Exhibiting an Atopic Dermatitis Phenotype 1.1 Validation of the Experiment Treatment of keratinocytes by the combination of poly(I:C) and Th1/Th2 cytokines (IL4, IL13, TNF) clearly induced an atopic dermatitis phenotype by inducing the expression of various characteristic genes involved in the pathology.

Indeed, an increase in expression of the innate immunity marker S100A7, cytokines (TSLP, IL1A, IFN1a) and most of the chemokines studied (CCL3, CCL5, CCL7, CCL20, CCL22, CCL27 and IL8) was observed.

These effects were accompanied by an increase in transcription regulation markers RARRES3 and BCL3. At the same time, inhibition of markers involved in keratinocyte differentiation (KRT10, FLG, IVL and LASS6) is observed.

1.2 Effect of Compounds on the Atopic Dermatitis Model

The two compounds were tested at a concentration of 2.5 ng/ml (pure triptolide equivalent).

Root Extract (IBO.18.130)

The root extract has a moderate anti-inflammatory effect on this model by reversing the effects of the proinflammatory mixture. Indeed, expression of innate immunity marker S100A7, chemokines (CCL3, CCL5 and IL8) and oxidative stress marker (HMOX1) was suppressed whereas expression of the marker involved in keratinocyte differentiation, KRT10, was stimulated (table 1).

Plant Cell Culture Extract (IBO.18.134)

The plant cell culture (PCC) extract has a more marked anti-inflammatory effect than the root extract by suppressing expression of innate immunity markers S100A7 and RNASE7, cytokines TSLP and IL1A, chemokines (CCL3, CCL5 and IL8) and oxidative stress marker (HMOX1) (FIG. 9).

TABLE 1

Genes tested after induction of an atopic dermatitis phenotype

| Antimicrobial peptide, innate immunity | |
|---|---|
| TLR3 | Toll-like receptor 3 |
| S100A7 | S100 calcium binding protein A7 |
| S100A11 | S100 calcium binding protein A11 |
| RNASE7 | Ribonuclease, RNase A family, 7 |
| CAMP | Cathelicidin antimicrobial peptide |

| Interleukins | |
|---|---|
| TSLP | Thymic stromal lymphopoietin |
| IL1A | Interleukin 1, alpha |
| IL18 | Interleukin 18 (interferon-gamma-inducing factor) |
| IFNA2 | Interferon, alpha 2 |
| IFNB1 | Interferon, beta 1, fibroblast |
| IL4R | Interleukin 4 receptor |

| Chemokines | |
|---|---|
| IL8 | Interleukin 8 |
| CCL3 | Chemokine (C-C motif) ligand 3 |
| CCL5 | Chemokine (C-C motif) ligand 5 |
| CCL7 | Chemokine (C-C motif) ligand 7 |
| CCL11 | Chemokine (C-C motif) ligand 11 |
| CCL13 | Chemokine (C-C motif) ligand 13 |
| CCL17 | Chemokine (C-C motif) ligand 17 |
| CCL20 | Chemokine (C-C motif) ligand 20 |
| CCL22 | Chemokine (C-C motif) ligand 22 |
| CCL27 | Chemokine (C-C motif) ligand 27 |

| Keratinocyte differentiation | |
|---|---|
| IVL | Involucrin |
| CDSN | Corneodesmosin |
| FLG | Filaggrin |
| LOR | Loricrin |
| KRT10 | Keratin 10 |
| LASS6 | LAG1 homolog, ceramide synthase 6 |

| Transcriptional regulation | |
|---|---|
| RARRES3 | Retinoic acid receptor responder (tazarotene induced) 3 |
| BCL3 | B-cell CLL/lymphoma 3 |

| Oxidative stress response | |
|---|---|
| HMOX1 | Heme oxygenase (decycling) 1 |

2. Effects of Compounds on Keratinocytes Exhibiting a Psoriasis Phenotype 2.1 Validation of the Experiment Treatment of keratinocytes by the cytokine mixture (oncostatin M+IL17+TNF) clearly induced a psoriatic phenotype by inducing the expression of various characteristic genes involved in the pathology.

The cytokine mixture induces an increase in the expression of genes coding for antimicrobial peptides or involved in innate immunity (CAMP, DEFB103A, DEFB4, PI3, S100A7, S100A7A, SPLI and TLR2), chemotaxis (CCL5, CXCL5, CXCL10 and IL8), inflammation (IL1B), extracellular matrix degradation (MMP1 and MMP3) and cell defense against oxidative stress (HMOX1). At the same time, inhibition of markers involved in differentiation (KRT1, KRT10 and FLG) and cell cohesion (DSG1 and CALML5) is observed.

2.2 Effect of Compounds on the Psoriasis Model

Both compounds were tested at concentrations of 2.5 ng/ml (pure triptolide concentration equivalent).

Root Extract (IBO.18.130)

The root extract has an anti-inflammatory effect on this model. Indeed, 10 genes induced by the cytokine cocktail are suppressed by the extract. A dose-dependent effect on certain genes can also be observed (FIG. 10).

Plant Cell Culture Extract (IBO.18.134)

The plant cell culture (PCC) extract also has an anti-inflammatory effect on this model. Indeed, 13 genes induced by the cytokine cocktail are suppressed by the extract by a factor greater than two. The anti-inflammatory effect on the psoriasis model is more marked with the plant culture extract than the root extract (FIG. 10).

TABLE 2

Genes tested after induction of a psoriasis phenotype

Keratinocyte differentiation

| | |
|---|---|
| CALML5 | Calmodulin-like 5 |
| FABP5 | Fatty acid binding protein 5 (psoriasis-associated) |
| FLG | Filaggrin |
| KRT1 | Keratin 1 |
| KRT10 | Keratin 10 |
| LOR | Loricrin |
| SPRR1A | Small proline-rich protein 1A |
| SPRR2A | Small proline-rich protein 2A |
| TGM1 | Transglutaminase 1 |

Antimicrobial peptide, innate immunity

| | |
|---|---|
| CAMP | Cathelicidin antimicrobial peptide |
| DEFB103A | Defensin, beta 103A |
| DEFB4 | Defensin, beta 4 |
| PI3 | Peptidase inhibitor 3, skin-derived |
| RNASE7 | Ribonuclease, RNase A family, 7 |
| S100A7 | S100 calcium binding protein A7 |
| S100A7A | S100 calcium binding protein A7A |
| SLPI | Secretory leukocyte peptidase inhibitor |
| TLR2 | Toll-like receptor 2 |

Chemokines

| | |
|---|---|
| CCL5 | Chemokine (C-C motif) ligand 5 |
| CXCL10 | Chemokine (C-X-C motif) ligand 10 |
| CXCL5 | Chemokine (C-X-C motif) ligand 5 |
| IL8 | Interleukin 8 |

Interleukins

| | |
|---|---|
| IL1B | Interleukin 1, beta |

Cell-cell interactions

| | |
|---|---|
| CDSN | Corneodesmosin |
| DSG1 | Desmoglein 1 |
| CEACAM1 | Carcinoembryonic antigen-related cell adhesion molecule 1 |

Oxidative stress response

| | |
|---|---|
| HMOX1 | Heme oxygenase (decycling) 1 |

Matrix degradation/Wound healing

| | |
|---|---|
| MMP1 | Matrix metallopeptidase 1 (interstitial collagenase) |
| MMP3 | Matrix metallopeptidase 3 (stromelysin 1, progelatinase) |

STAT signaling

| | |
|---|---|
| SOCS3 | Suppressor of cytokine signaling 3 |

Conclusion on the Two Models

Under the experimental conditions of this test, extracts IBO.18.130 (root extract) and IBO.18.134 (plant culture extract) had an anti-inflammatory effect in the in vitro models of atopic dermatitis and psoriasis induced in keratinocytes. This effect is more marked with the plant culture extract compared to the root extract in pure triptolide equivalent.

Cytotoxicity Tests

Comparison of cytotoxicity of three compounds: TRP (MP0001128), root extract (IBO.18.130) and PCC extract (IBO.18.134) with identical TRP concentrations.

NHEK cells are seeded in black 96-well microplates and incubated at 37° C. with 5% $CO_2$ for 24 hours.

The 96-well microplates are centrifuged for 10 minutes at 1200 rpm.

ATPlite Assay

50 µl of lysis buffer is added to the black microplate, and after agitation 50 µl of substrate is added and luminescence is read with a TopCount counter.

LDH Assay

100 µl of supernatant is taken from the black microplate and deposited in a transparent microplate. After adding 100 µl of LDH assay solution the plate is incubated for 30 minutes at room temperature, away from light. The colorimetric reaction of the LDH assay is stopped with 50 µl of 1 N HCl. Cytolysis is analyzed by reading absorbance on an EnVision reader at 485 nm.

NHEK cells are brought together with increasing concentrations of the various compounds.

The results obtained by the LDH and ATPlite assays clearly show greater cytotoxicity with IBO.18.130 (root extract) compared to IBO.18.134 (plant culture extract) and to MP00011128 (pure triptolide). (See FIG. 11.)

The invention claimed is:

1. A method for producing a triptolide-enriched extract comprising:
   (i) producing a biomass of dedifferentiated cells derived from calluses of the species *Tripterygium* in nutrient media under biomass growth conditions to produce a cell culture;
   (ii) eliminating hormones from the cell culture obtained in step (i) by culturing said cells in an elimination medium substantially free of auxins;
   (iii) adding an elicitation cocktail to the elimination medium containing the cells of step (ii) then further culturing the cells therein, wherein the elicitation cocktail comprises:
      a) at least one cellular differentiation factor of plant cells, selected from the group consisting of cytokinins and gibberellins,
      b) at least one stressing agent selected from the group consisting of 5-chlorosalicylic acid (5-chloro SA), salicylic acid, acetylsalicylic acid (ASA) and methyl jasmonate (MeJA), and
      c) at least one precursor of the terpene synthesis pathway selected from the group consisting of geraniol, farnesol, sodium acetate, pyruvic acid or mevalonic acid; and
   (iv) obtaining said triptolide-enriched extract from the elimination medium following step (iii).

2. The method of claim 1, wherein the cellular differentiation factor of plant cells is selected from the cytokinins.

3. The method of claim 1, wherein the elicitation cocktail comprises a stressing agent, wherein the stressing agent consists of 5-chlorosalicylic acid, acetylsalicylic acid or salicylic acid, and methyl jasmonate.

4. The method of claim 1, wherein the elimination medium contains no auxin.

5. The method of claim 1, wherein the hormonal elimination step (ii) lasts for 5-15 days.

6. The method of claim 1, wherein step (iii) lasts for 15-35 days.

7. The method of triptolide production of claim 1, wherein step(i) proceeds with agitation for 10-30 days at roughly 27-28°C.

8. The method of triptolide production, of claim 1, wherein the elicitation cocktail contains benzylaminopurine, 5-chlorosalicylic acid, acetylsalicylic acid or salicylic acid, methyl jasmonate, farnesol and geraniol.

9. The method of triptolide production of claim 1, wherein the triptolide concentration of the culture supernatants after step (iii) is greater than 50 mg/liter of culture medium.

10. The method of triptolide production of claim 1, wherein step (iv) is liquid/liquid extraction.

11. A method of culturing cells of the species *Tripterygium* which comprises culturing cells of the species *Tripterygium* in a culture medium containing an elicitation cocktail comprising:
- a) at least one cellular differentiation factor of plant cells selected from the group consisting of cytokinins and gibberellins,
- b) at least one stressing agent selected from the group consisting of 5-chlorosalicylic acid (5-chloro SA), salicylic acid, acetylsalicylic acid (ASA) and methyl jasmonate(MeJA), and
- c) at least one precursor of the terpene synthesis pathway selected from the group consisting of geraniol farnesol, sodium acetate pyruvic acid and mevalonic acid.

12. The method according to claim 11, wherein said elicitation cocktail comprises: 0.7-3 mg/l benzylaminopurine (BAP); 3-5 mg/l 5-chlorosalicylic acid (5-chloro SA); 33-45 mg/l acetylsalicylic acid (ASA); 22.4-24mg/l methyl jasmonate (MeJA); 20-30 geraniol; and 19-30 mg/l farnesol (F—OH); with mg/l expressing mg/l of culture medium.

13. The method of claim 4, wherein the elimination medium contains no 2,4-dichlorophenoxyacetic acid (2,4-D) or naphthalene acetic acid (NAA).

14. The method of claim 5, wherein the hormonal elimination step (ii) lasts for 7 days.

15. The method of claim 6, wherein the elicitation phase step (iii) lasts for 20-25 days.

\* \* \* \* \*